US011279721B2

(12) United States Patent
Chen et al.

(10) Patent No.: US 11,279,721 B2
(45) Date of Patent: Mar. 22, 2022

(54) MANGANESE (II) COMPLEX, PREPARATION METHOD THEREOF, AND USE THEREOF IN ORGANIC LIGHT EMITTING DIODES

(71) Applicant: FUJIAN INSTITUTE OF RESEARCH ON THE STRUCTURE OF MATTER, CHINESE ACADEMY OF SCIENCES, Fujian (CN)

(72) Inventors: Zhongning Chen, Fujian (CN); Liangjin Xu, Fujian (CN); Jinyun Wang, Fujian (CN)

(73) Assignee: FUJIAN INSTITUTE OF RESEARCH ON THE STRUCTURE OF MATTER, CHINESE ACADEMY OF SCIENCES, Fujian (CN)

( * ) Notice: Subject to any disclaimer, the term of this patent is extended or adjusted under 35 U.S.C. 154(b) by 456 days.

(21) Appl. No.: 16/313,863

(22) PCT Filed: May 19, 2017

(86) PCT No.: PCT/CN2017/085149
§ 371 (c)(1),
(2) Date: Dec. 27, 2018

(87) PCT Pub. No.: WO2018/000984
PCT Pub. Date: Jan. 4, 2018

(65) Prior Publication Data
US 2019/0144478 A1    May 16, 2019

(30) Foreign Application Priority Data

Jun. 28, 2016 (CN) .......................... 201610487014.X

(51) Int. Cl.
*C07F 13/00* (2006.01)
*C09K 11/06* (2006.01)
*C07C 211/63* (2006.01)
*C07F 9/572* (2006.01)
*C07F 9/54* (2006.01)
*H01L 51/00* (2006.01)
*H01L 51/50* (2006.01)

(52) U.S. Cl.
CPC .......... *C07F 13/005* (2013.01); *C07C 211/63* (2013.01); *C07F 9/54* (2013.01); *C07F 9/572* (2013.01); *C07F 13/00* (2013.01); *C09K 11/06* (2013.01); *H01L 51/0037* (2013.01); *H01L 51/0059* (2013.01); *H01L 51/0067* (2013.01); *H01L 51/0072* (2013.01); *H01L 51/0084* (2013.01); *H01L 51/5012* (2013.01); *H01L 51/5092* (2013.01); *H01L 51/5056* (2013.01); *H01L 51/5072* (2013.01)

(58) Field of Classification Search
CPC ........ C07F 13/005; C07F 13/00; C07F 9/572; C07F 9/54; C07F 9/5728; C07F 9/5442; C09K 11/06; C09K 2211/10; C09K 2211/1029; C09K 2211/1014; C09K 2211/188; C07C 211/63; C07C 13/00; H01L 51/0037; H01L 51/0059; H01L 51/0067; H01L 51/0072; H01L 51/0084; H01L 51/5012; H01L 51/5092; H01L 51/5056; H01L 51/5072; H01L 51/5016; H01L 51/005; H01L 51/0077; H01L 51/56
USPC .................. 428/690, 691; 427/58, 64, 66
See application file for complete search history.

(56) References Cited

U.S. PATENT DOCUMENTS

| | | | | |
|---|---|---|---|---|
| 2008/0000032 A1* | 1/2008 | Wieprecht | ............ | C11D 3/3932 8/111 |
| 2009/0011929 A1* | 1/2009 | Ishiyama | .............. | C07D 403/14 502/167 |
| 2010/0222577 A1* | 9/2010 | Small | ...................... | B01J 31/226 544/64 |
| 2011/0071066 A1* | 3/2011 | Wagner | .................. | C11D 3/323 510/237 |
| 2020/0087331 A1* | 3/2020 | White | .................... | C07J 1/0096 |

FOREIGN PATENT DOCUMENTS

CN     105601671 A    5/2016

OTHER PUBLICATIONS

N. Islam, "Optical Spectra of Manganese (II) Bromide in Molten tetra-n-Butylphosphonium Bromide", Applied Spectroscopy, 29 (3), 1975, 266-268. (Year: 1975).*
Elena I. Zhilyaeva et al., "Phase Transitions In θ-(ET)4MnBr4(C6H6—nCln)(n = 1,2) driven by ordering in anion and/or cation layers", CrystEngComm, vol. 16, Sep. 20, 2014, p. 10103-10111.
James L. Painter et al., "Phosphorescence in Molten Tetrabutylammonium Tribromomanganate", J. Coord Chem, vol. 13, Dec. 13, 2006, pp. 185-196.
Rolf W. Saalfrank et al., "Synthesis and Characterization of Metal-Centered, Six-Membered, Mixed-Valent, Heterometallic Wheels of Iron, Manganese, and Indium", Chemistry: A European Journal, vol. 12, Feb. 9, 2006, pp. 2428-2433.
(Continued)

*Primary Examiner* — Douglas J McGinty
(74) *Attorney, Agent, or Firm* — Novick, Kim & Lee, PLLC; Allen Xue

(57) ABSTRACT

The invention relates to a manganese (II) complex, its preparation method and use. The structure of the complex is (R1R2R3R4A)2[MnX4], wherein R1, R2, R3 and R4 are identical or different, independently selected from alkyl, aryl, or heteroaryl; said alkyl, aryl, or heteroaryl can be optionally substituted with a substituent, and the substituent is preferably alkyl, aryl or heteroaryl; A is N, P, or As; X is optionally F, Cl, Br, or I. The present invention also relates to an organic light emitting diode, its preparation method and use, wherein the manganese (II) complex of the invention is used as a dopant in the light-emitting layer. The prepared organic light emitting diode exhibits high electrical-to-optical conversion efficiency which can be used for flat-panel displays and illuminations.

13 Claims, 1 Drawing Sheet

(56) References Cited

OTHER PUBLICATIONS

E. Styczen et al., "Thermal analysis of manganese(II) complexes of general formula (Et4N)2[MnBrnCl4—n]", Thermochimica Acta, 503-504, 2010, pp. 21-27.
E. Styczen et al., "Thermal analysis of manganese(II) complexes of general formula (Bu4N)2[MnBrnCl4—n]", Thermochimica Acta, vol. 481, 2009, pp. 46-51.

* cited by examiner

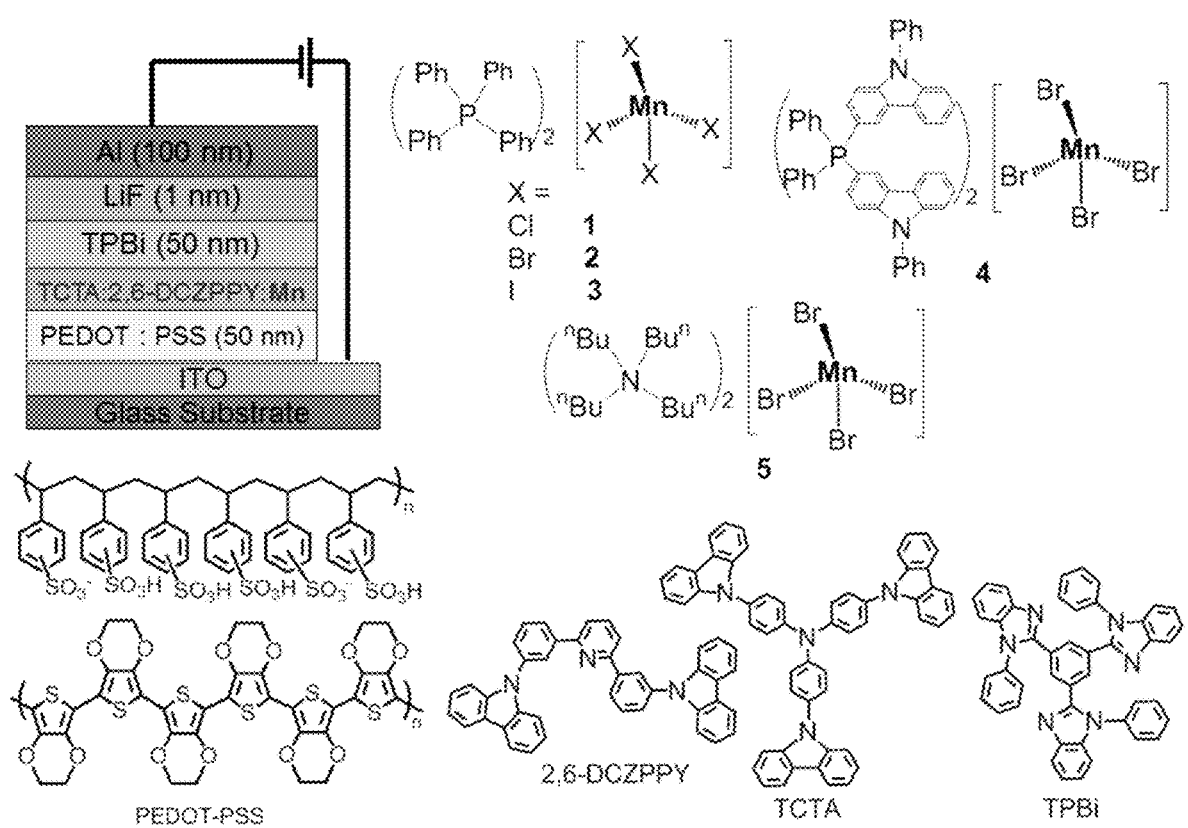

MANGANESE (II) COMPLEX, PREPARATION METHOD THEREOF, AND USE THEREOF IN ORGANIC LIGHT EMITTING DIODES

TECHNICAL FIELD

The present invention relates to the field of organic light emitting diodes, which can be used in the field of full-color flat-panel displays and lighting. In particular, the present invention relates to a green light-emitting manganese (II) complex, a preparation method thereof, and applications of the same in organic light emitting diode.

BACKGROUND ART

Organic electroluminescence refers to the phenomenon in which electrical energy is directly converted into light energy using organic light emitting diodes (OLEDs) at a low DC voltage in the range from 3V to 12 V, which is broadly applied in the field of flat panel displays and lighting. Compared to traditional lighting and display technologies, organic electroluminescence has many advantages such as full-color display, wide viewing angle, high resolution, fast response, low power consumption, high efficiency, and low temperature resistance and so on; and organic light emitting devices have excellent characteristics such as simple structures, ultra-lightness, ultra-thinness, good flexibility, and foldability and so on.

The key feature of organic light emitting diodes relies on light-emitting thin film materials. At present, most of the phosphorescent materials used in commercial organic electroluminescent devices are charge-neutral cyclometalated iridium (III) complexes, which are doped into organic host materials to form light-emitting layers. Currently, large-scale commercial applications of organic light emitting diodes are restrained from three aspects: 1) iridium is a precious metal with very limited content in earth (iridium is one of the least abundant metal elements in earth with annual production of only 3 tons in the world); 2) the light-emitting layers with the charge-neutral cyclometalated iridium (III) complexes are fabricated through vacuum thermal evaporation deposition process, leading to higher manufacturing costs and difficulties in manufacturing large-area devices; 3) the stable operation time of blue light-emitting devices needs to be increased. In response to these challenges, for the first time, the phosphorescent noble-metal iridium (III) materials are replaced with the luminescent metal manganese (II) materials in the present invention, which are earth-abundant, cheap, and environmentally friendly, and high-performance and low-cost green organic light-emitting diodes are achieved.

CONTENTS OF THE INVENTION

An object of the present invention is to provide a manganese (II) complex, and its use in organic light emitting diodes.

Another object of the present invention is to provide an organic light emitting diode comprising the manganese (II) complex.

Objects of the present invention can be realized by the following method.

A manganese (II) complex, wherein the chemical structure of the complex is $(R_1R_2R_3R_4A)_2[MnX_4]$;

wherein $R_1$, $R_2$, $R_3$ and $R_4$ are identical or different, and $R_1$, $R_2$, $R_3$ and $R_4$ are independently selected from alkyl, aryl, or heteroaryl; the alkyl, the aryl, or the heteroaryl may be optionally substituted with a substituent, and the substituent is preferably an alkyl group, an aryl group or a heteroaryl group;

A is N, P, or As;

X is optionally F, Cl, Br, or I. The alkyl/alkyl group is a linear or branched alkyl group having 1 to 10 (preferably 1 to 6) carbon atoms. Representative alkyl/alkyl group comprises methyl, ethyl, n-propyl, isopropyl, n-butyl, t-butyl, etc.

The aryl/aryl group is a monocyclic or polycyclic aromatic group having 6 to 20 carbon atoms. Representative aryl/aryl group comprises phenyl, naphthyl, etc.

The heteroaryl/heteroaryl group is a monocyclic or polycyclic heteroaromatic group having 1 to 20 carbon atoms containing at least one, preferably one to four, of heteroatoms selected from N, S or O. Representative heteroaryl/heteroaromatic group comprises pyrrolyl, pyridyl, pyrimidinyl, imidazolyl, thiazolyl, oxazolyl, oxadiazolyl, carbazolyl, quinolyl, quinozolinyl, indolyl, etc.

According to the present invention, the chemical structure of the manganese (II) complex is represented by the following formula (I):

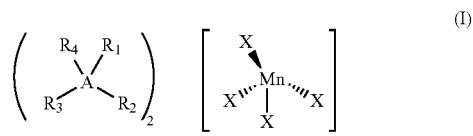

(I)

In an embodiment, when A is N, $R_1$, $R_2$, $R_3$ and $R_4$ are not butyl at the same time.

According to the present invention, preferably, $R_1$, $R_2$, $R_3$ and $R_4$ are independently selected from alkyl, aryl, arylalkyl, heteroaryl, or arylheteroaryl; more preferably, $R_1$, $R_2$, $R_3$ and $R_4$ are independently selected from ethyl, n-butyl, phenyl, benzyl, carbazyl, or phenylcarbazyl.

In an embodiment of the present invention, $R_1$ and $R_2$ are identical; $R_3$ and $R_4$ are identical.

In another embodiment of the present invention, $R_1$, $R_2$, $R_3$ and $R_4$ are all identical.

According to the present invention, preferably, A is N or P.

According to the present invention, the manganese (II) complex is selected from the following compounds:

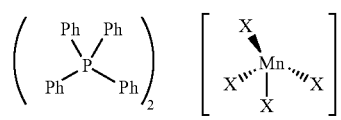

X =
Cl  1
Br  2
I   3

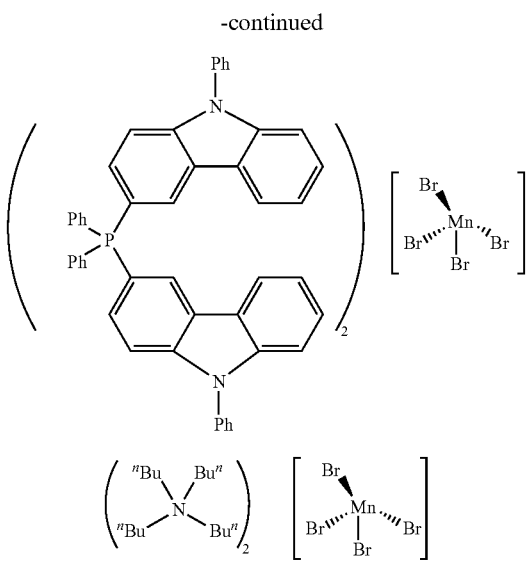

compound 1: $R_1$, $R_2$, $R_3$ and $R_4$ are identical and are phenyl; A is P; X is Cl;

compound 2: $R_1$, $R_2$, $R_3$ and $R_4$ are identical and are phenyl; A is P; X is Br;

compound 3: $R_1$, $R_2$, $R_3$ and $R_4$ are identical and are phenyl; A is P; X is I;

compound 4: $R_1$ and $R_2$ are identical and are 9-carbazyl; $R_3$ and $R_4$ are identical and are phenyl; A is P; X is Br;

compound 5: $R_1$, $R_2$, $R_3$ and $R_4$ are identical and are n-butyl; A is N; X is Br.

A method for preparing the manganese (II) complex is also provided in the present invention, comprising the following steps: mixing $MnX_2$ and $(R_1R_2R_3R_4A)X$ in a solvent to obtain the manganese (II) complex, wherein $R_1$, $R_2$, $R_3$, $R_4$, A and X are as defined above.

According to the present invention, the solvent is preferably alcohol or halogenated hydrocarbon, such as methanol or dichloromethane.

According to the present invention, in the method, the molar ratio of $MnX_2$:$(R_1R_2R_3R_4A)X$ is 1.5-2.5:0.5-1.5, preferably 1:2.

According to the present invention, the reaction is carried out at room temperature. Preferably, after completion of the reaction, the product is purified by recrystallization. The solvent used in recrystallization is preferably petroleum ether and dichloromethane.

The manganese (II) complex of the present invention exhibits strong phosphorescence in solution, crystal, and thin film states. It can be used as a dopant in a light-emitting layer, which is applicable in organic light emitting diodes.

Use of the manganese (II) complex in organic light emitting diodes is also provided in the present invention.

Further, an organic light emitting diode, comprising a light-emitting layer, wherein the light-emitting layer comprises the manganese (II) complex, is also provided in the present invention. The organic light emitting diode exhibits superior green electroluminescence performance.

According to the present invention, in the light-emitting layer, a weight percentage of the manganese (II) complex of the present invention is 0-50%, preferably 10-30%. Further preferably, a light-emitting layer is formed by doping 20% by weight of the manganese (II) complex of the present invention into host materials.

According to the present invention, structures of the organic light emitting diode may be various known in the prior art. Preferably, it comprises an anode layer, a hole injection layer, a hole transport layer, a light-emitting layer, an electron transport layer, an electron injection layer and a cathode layer. The hole injection layer and the hole transport layer are PEDOT:PSS (PEDOT:PSS=poly(3,4-ethyleneoxythiophene)-poly(styrene sulfonate)). The light-emitting layer comprises the manganese (II) complex of the present invention and a substance having a hole-transport property, such as one or more selected from TCTA (tris(4-(9H-carbazol-9-yl)phenyl)amine), mCP (1,3-bis(9-carbazolyl)benzene), CBP (4,4'-bis(9H-carbazol-9-yl)-1,1'-biphenyl) or 2,6-DCZPPY (2,6-bis (3-(9H-carbazol-9-yl)phenyl)pyridine). The electron transport layer may be TPBi (1,3,5-tris (1-phenyl-1H-benzo[d]imidazole-2-yl)phenyl), BmPyPB (3,3'',5,5''-tetra(pyridin-3-yl)-1,1':3',1''-terphenyl), BCP (2,9-dimethyl-4,7-diphenyl-1,10-phenanthroline) or OXD-7 (2,2'-(1,3-phenylene) bis[5-(4-tert-butylphenyl)-1,3,4-oxadiazole]. The electron injection layer is LiF. The cathode layer is Al.

According to the present invention, the device structure is preferably ITO/PEDOT:PSS (50 nm)/40% TCTA: 40% 2,6-DCZPPY: 20% wt of the manganese (II) complex (50 nm) of the invention/TPBi (50 nm)/LiF (1 nm)/Al (100 nm), wherein ITO is an indium tin oxide conductive film, PEDOT:PSS is poly(3,4-ethyleneoxythiophene)-poly(styrene sulfonate), TCTA is tris(4-(9H-carbazol-9-yl)phenyl) amine, 2,6-DCZPPY is 2,6-bis (3-(9H-carbazol-9-yl)phenyl)pyridine, and TPBi is 1,3,5-tris(1-phenyl-1H-benzo[d]imidazole-2-yl)phenyl.

A method for preparing the organic light emitting diode is also provided, comprising: 1) fabricating a hole injection layer/a hole transport layer of the organic light emitting diode on an anode through solution process; 2) fabricating a light-emitting layer doped with the manganese (II) complex of the present invention through solution process; 3) fabricating an electron transport layer, an electron injection layer and a cathode layer in sequence through vacuum thermal evaporation deposition process.

In a preferred embodiment of the present invention, the method comprises: firstly, fabricating a hole injection layer and a hole transport layer by using aqueous PEDOT:PSS on an anode; furthermore, fabricating a light-emitting layer by doping the blended host materials of hole-transport TCTA and 2,6-DCZPPY with the manganese (II) complex of the present invention; and then fabricating a TPBi electron transport layer, a LiF electron injection layer and an Al cathode layer in sequence through vacuum thermal evaporation deposition process.

According to the present invention, in the method, the PEDOT:PSS hole injection layer/hole transport layer and the TCTA: 2,6-DCZPPY light-emitting layer are fabricated using a solution-based spin-coating method, and the TPBi electron transport layer and LiF electron injection layer are fabricated through vacuum thermal evaporation deposition process, respectively.

The organic light emitting diode prepared from the phosphorescent manganese (II) complex of the present invention has excellent performance, relatively high electrical-optical conversion efficiency, and the maximum quantum efficiency is larger than 2%.

Use of the organic light emitting diode is further provided, which can be used in the field of flat-panel displays and daily illuminations.

Compared with the prior art, the present invention has the following advantages:

1) The phosphorescent manganese (II) complex of the present invention exhibits strong phosphorescence emission in solid and thin films, wherein a quantum efficiency of the thin films is higher than 20%.

2) The organic light emitting diode is prepared by using the inexpensive phosphorescent manganese (II) complex instead of the noble metal ruthenium (III) complex in the present invention as a dopant in the light-emitting layer, which dramatically reduces the production cost of the luminescent materials;

3) The hole injection layer/hole transport layer of the organic light emitting diode and the light-emitting layer are fabricated through solution process in the present invention, which can significantly reduce the cost of device fabrication.

DESCRIPTION OF THE DRAWING

FIG. 1 is the schematic representation of the device and the chemical structures of organic materials.

SPECIFIC EMBODIMENTS

In order to better explain the objects, technical solutions and technical effects, the present invention will be further illustrated with reference to the schemes and specific examples. However, those skilled in the art can readily understand that the following embodiments are not intended to limit the scope of the invention. Any improvement and modification based on the present invention are within the scope of the present invention.

Example 1: Preparation of $(Ph_4P)_2[MnCl_4]$ (1) Complex

To a solution of anhydrous $MnCl_2$ (47.3 mg, 0.1 mmol) in 10 mL of methanol was added a solution of $Ph_4PCl$ (50.6 mg, 0.2 mmol) in 10 mL of methanol. After being stirred for 4 hours, the reaction solution was dried in vacuum. The obtained solid was dissolved in 5 mL of dichloromethane, and filtered to give a transparent filtrate. At room temperature, recrystallization by slow diffusion of petroleum ether into a dichloromethane solution afforded pale green crystals. Yield: 92%. Elemental analysis $(C_{48}H_{40}C_{14}P_2Mn)$, calculated data: C, 65.85; H, 4.60. Found: C, 65.56; H, 4.57. IR (KBr, cm$^{-1}$): 3843, 3741, 3633, 3517, 3057, 1625, 1586, 1484, 1437, 1315, 1111, 993, 766, 727, 687, 527.

Example 2: Preparation of $(Ph_4P)_2[MnBr_4]$ (2) Complex

The preparation method was basically the same as that described in Example 1, except that anhydrous $MnCl_2$ was replaced by anhydrous $MnBr_2$, and $Ph_4PCl$ was replaced by $Ph_4PBr$. Yield: 95%. Elemental analysis $(C_{48}H_{40}Br_4P_2Mn)$, calculated data: C, 54.73; H, 3.83. Found: C, 54.25; H, 3.78. IR (KBr, cm$^{-1}$): 3850, 3736, 3473, 3051, 1621, 1587, 1483, 1107, 996, 758, 724, 692, 528.

Example 3: Preparation of $(Ph_4P)_2[MnI_4]$ (3) Complex

The preparation method was basically the same as that described in Example 1, except that anhydrous $MnCl_2$ was replaced by anhydrous $MnI_2$, and $Ph_4PCl$ was replaced by $Ph_4PI$. Yield: 75%. Elemental analysis $(C_{48}H_{40}I_4P_2Mn)$, calculated data: C, 46.40; H, 3.25. Found: C, 46.90; H, 3.28. IR (KBr, cm$^{-1}$): 3847, 3454, 3057, 1625, 1585, 1485, 1437, 1385, 1313, 1110, 997, 759, 724, 689, 526, 448.

Example 4: Preparation of $[Ph_2P(Carbazol-9-Yl)_2]_2[MnBr_4]$ (4) Complex

The preparation method was basically the same as that described in Example 2, except that anhydrous $Ph_2PBr$ was replaced by synthesized $Ph_2P(carbazol-9-yl)_2Br$. Yield: 78%. Elemental analysis $(C_{72}H_{54}Br_4N_2P_2Mn)$, calculated data: C, 62.50; H, 3.93; N, 2.02. Found: C, 65.26; H, 3.90; N, 2.11. IR (KBr, cm$^{-1}$): 3860, 3754, 3470, 3055, 1628, 1581, 1484, 1422, 1391, 1112, 998, 757, 729, 671, 526.

Example 5: Preparation of $[(n-Bu)_4N]_2[MnBr_4]$ (5) Complex

The preparation method was basically the same as that described in Example 2, except that anhydrous $Ph_2PBr$ was replaced by $(n-Bu)_4NBr$. Yield: 87%. Elemental analysis $(C_{32}H_{72}Br_4N_2Mn)$, calculated data: C, 44.72; H, 8.44; N, 3.26. Found: C, 44.56; H, 8.26; N, 3.38. IR (KBr, cm$^{-1}$): 3465, 3423, 2958, 2868, 1486, 1387, 1155, 1033, 873, 747.

Example 6: Photoluminescence Performance Measurement

The excitation spectra, the emission spectra, the luminescence lifetimes and the luminescence quantum yields of the complex 1-5 crystals prepared in Examples 1-5 and the thin films of 40% TCTA: 40% 2,6-DCZPPY: 20% of the manganese (II) complexes of Examples 1-5 (by weight) were measured on Edinburgh FLS920 fluorescence spectrometer, respectively. The luminescence quantum yields of the crystal samples were determined by using a 142 mm-diameter integrating sphere. The luminescence quantum yields of the thin films of 40% TCTA: 40% 2,6-DCZPPY: 20% of the manganese (II) complexes of Examples 1-5 (by weight) (the thin films are prepared by spin-coating dichloromethane solutions of the above materials) are determined on the 142 mm-diameter integrating sphere.

The complexes 1-5 in Examples 1-5 exhibit strong phosphorescence emissions in crystals and thin films. The emission wavelengths, the emission lifetimes and the quantum yields are listed in Table 1.

TABLE 1

Photoluminescence emission wavelengths, emission lifetimes and quantum yields of the complex 1-5 of the present invention

| | Crystal | | | Thin film | | |
|---|---|---|---|---|---|---|
| Complex | $\lambda_{em}$ [nm] | $\tau_{em}$ [µs] | $\Phi_{em}$ [%] | $\lambda_{em}$ [nm] | $\tau_{em}$ [µs] | $\Phi_{em}$ [%] |
| 1 | 517 | 1339 | 75.7 | 517 | 1365 | 24.4 |
| 2 | 515 | 357 | 98.5 | 521 | 317 | 71.2 |
| 3 | 529 | 158 | 29.3 | 521 | 305 | 31.7 |
| 4 | 520 | 127.9 | 8.6 | 519 | 172.9 | 45.2 |
| 5 | 518 | 352.4 | 71.3 | 518 | 415.5 | 31.5 |

Example 7: Fabrication of Organic Light Emitting Diodes and Electroluminescence Performance Measurement The organic light emitting diodes were fabricated by using 20% by weight of the phosphorescent complexes 1-5 prepared in Examples 1-5 as luminescent materials doped into the blended host materials of TCTA (40%): 2,6-DCZPPY (40%) in the light-emitting layers, respectively. The device structures were preferably ITO/PEDOT:PSS (50 nm)/40% TCTA: 40% 2,6-DCZPPY: 20% wt of the manganese (II) complexes 1-5 (50 nm) in Examples 1-5/TPBi (50 nm)/LiF (1 nm)/Al (100 nm).

Firstly, the ITO substrates were cleaned by using deionized water, acetone and isopropanol, respectively, followed by UV-Ozone treatment for 15 min. The filtered aqueous solution of PEDOT:PSS was spin coated onto the ITO substrates at 3000 rpm, dried at 140° C. for 20 min to afford 50 nm thick hole injection/hole transport layers. Then the filtered solution of 40% TCTA: 40% 2,6-DCZPPY: 20% wt of the manganese (II) complexes 1-5 in Examples 1-5 (percentage by weight) in dichloromethane was spin coated onto the PEDOT:PSS thin films to form 50 nm thick light emitting layers. After that, the ITO substrates were loaded into a vacuum deposition chamber with a pressure of less than $4\times10^{-4}$ Pa, and were subsequently thermally deposited with 50 nm thick TPBi electron transport layers, 1 nm thick LiF electron injection layers and 100 nm thick Al cathodes.

The LED device performance was determined at room temperature in the dry ambient air. The parameters of the electroluminescence performance of the manganese (II) complexes 1-5 prepared in Examples 1-5, including electroluminescence emission wavelength ($\lambda_{EL}$), turn-on voltage ($V_{on}$), maximum luminance ($L_{max}$), maximum current efficiency ($CE_{max}$), maximum power efficiency ($PE_{max}$), and maximum external quantum efficiency ($EQE_{max}$), are listed in Table 2.

TABLE 2

Electroluminescence performance data of the phosphorescent manganese (II) complex 1-5 of the present invention

| Complex | $\lambda_{EL}$ [nm] | $V_{on}$[a] [V] | $L_{max}$[b] [cd/m$^2$] | $CE_{max}$[c] [cd/A] | $PE_{max}$[d] [lm/W] | $EQE_{max}$[e] [%] |
|---|---|---|---|---|---|---|
| 1 | 527 | 5.9 | 958 | 8.2 | 3.2 | 2.2 |
| 2 | 521 | 4.8 | 2340 | 32.1 | 16.2 | 9.6 |
| 3 | 531 | 5.5 | 1229 | 17.6 | 8.1 | 4.8 |
| 4 | 520 | 6.4 | 2083 | 23.7 | 9.4 | 6.8 |
| 5 | 528 | 5.5 | 1089 | 17.3 | 8.1 | 4.6 |

[a] turn-on voltage ($V_{on}$) at luminance of 1 cd/m$^2$,
[b] maximum luminance,
[c] maximum current efficiency,
[d] maximum power efficiency, e) maximum external quantum efficiency.

The invention claimed is:

1. A manganese (II) complex of formula (I):

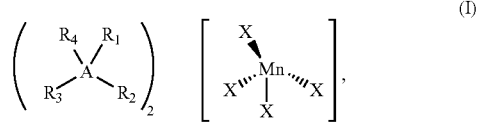

(I)

wherein $R_1$ and $R_2$ are identical and are 9-phenylcarbazyl, $R_3$ and $R_4$ are identical and are phenyl, A is P, and all four Xs are Br.

2. A method for preparing the manganese (II) complex according to claim 1, comprising the following steps: mixing MnX$_2$ and (R$_1$R$_2$R$_3$R$_4$A)X in a solvent to obtain the manganese (II) complex, wherein R$_1$, R$_2$, R$_3$, R$_4$, A and X are defined according to claim 1.

3. An organic light emitting diode, comprising a light-emitting layer that comprises a manganese (II) complex having a formula of (R$_1$R$_2$R$_3$R$_4$A)$_2$[MnX$_4$], wherein R$_1$, R$_2$, R$_3$ and R$_4$ are identical or different, and R$_1$, R$_2$, R$_3$ and R$_4$ are independently aryl or heteroaryl, which are unsubstituted or substituted with an alkyl group, an aryl group, or a heteroaryl group;

A is N, P, or As;

X is optionally F, Cl, Br, or I; and wherein alkyl is a linear or branched alkyl having 1 to 10 carbon atoms; the aryl is a monocyclic or polycyclic aromatic group having 6 to 20 carbon atoms; the heteroaryl is a monocyclic or polycyclic heteroaromatic group having 1 to 20 carbon atoms containing at least one heteroatoms selected from N, S or O.

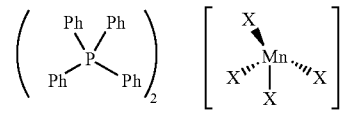

X =
Cl  1
Br  2
I   3

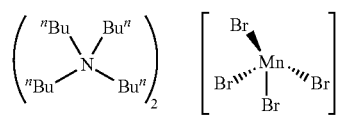

5

4. The organic light emitting diode according to claim 3, further comprising an anode layer, a hole injection layer/hole transport layer, an electron transport layer, an electron injection layer, and a cathode layer.

5. The organic light emitting diode according to claim 4, wherein the anode layer is indium tin oxide; the hole injection layer and the hole transport layer are PEDOT:PSS (PEDOT:PSS=poly(3,4-ethyleneoxythiophene)-poly(styrene sulfonate)); the light-emitting layer further comprises a substance having a hole-transport property selected from TCTA (tris(4-(9H-carbazol-9-yl)phenyl)amine), mCP (1,3-bis(9-carbazolyl)benzene), CBP (4,4'-bis(9H-carbazol-9-yl)-1,1'-biphenyl), 2,6-DCZPPY (2,6-bis (3-(9H-carbazol-9-yl)phenyl)pyridine), and mixtures thereof; the electron transport layer comprises TPBi (1,3,5-tris(1-phenyl-1H-benzo[d]imidazole-2-yl)phenyl), BmPyPB (3,3", 5,5"-tetra (pyridin-3-yl)-1,1':3',1"-terphenyl), BCP (2,9-dimethyl-4,7-diphenyl-1,10-phenanthroline), or OXD-7 (2,2'-(1,3-phenylene) bis[5-(4-tert-butylphenyl)-1,3,4-oxadiazole]; the electron injection layer is LiF; and the cathode layer is Al.

6. A method for preparing the organic light emitting diode according to claim 3, comprising: 1) fabricating a hole injection layer and a hole transport layer of the organic light emitting diode on an anode layer through solution process; 2) fabricating the light-emitting layer comprising the manganese (II) complex through solution process; and 3) fabricating an electron transport layer, an electron injection layer, and a cathode layer in sequence through vacuum thermal evaporation deposition process.

7. A display panel comprising a plurality of the organic light emitting diode according to claim 3.

8. A illumination device, comprising a plurality of the organic light emitting diode according to claim 3.

9. The organic light emitting diodes according to claim 3, wherein $R_1$, $R_2$, $R_3$, and $R_4$ are independently selected from aryl, heteroaryl, and arylheteroaryl.

10. The organic light emitting diodes according to claim 9, wherein $R_1$, $R_2$, $R_3$ and $R_4$ are independently selected from phenyl, carbazyl, and phenylcarbazyl.

11. The organic light emitting diodes according to claim 3, wherein A is N or P.

12. The organic light emitting diodes according to claim 3, wherein the manganese (II) complex is selected from compound 1, compound 2, compound 3, or compound 4,

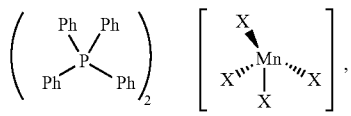

X =
Cl  1
Br  2
I   3

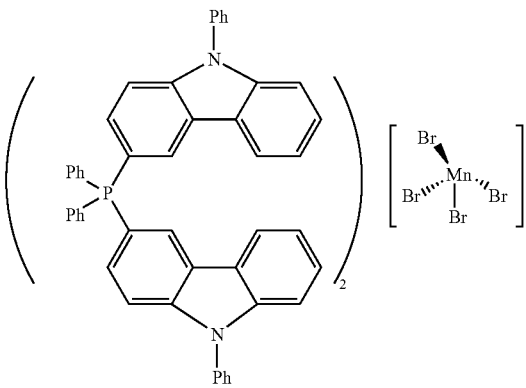

wherein, in compound 1, all four Xs are Cl;
wherein, in compound 2, all four Xs are Br; and
wherein, in compound 3, all four Xs are I.

13. The organic light emitting diode according to claim 6, wherein, in the light-emitting layer, a weight percentage of the manganese (II) complex is 5-50%.

* * * * *